Figure 1:
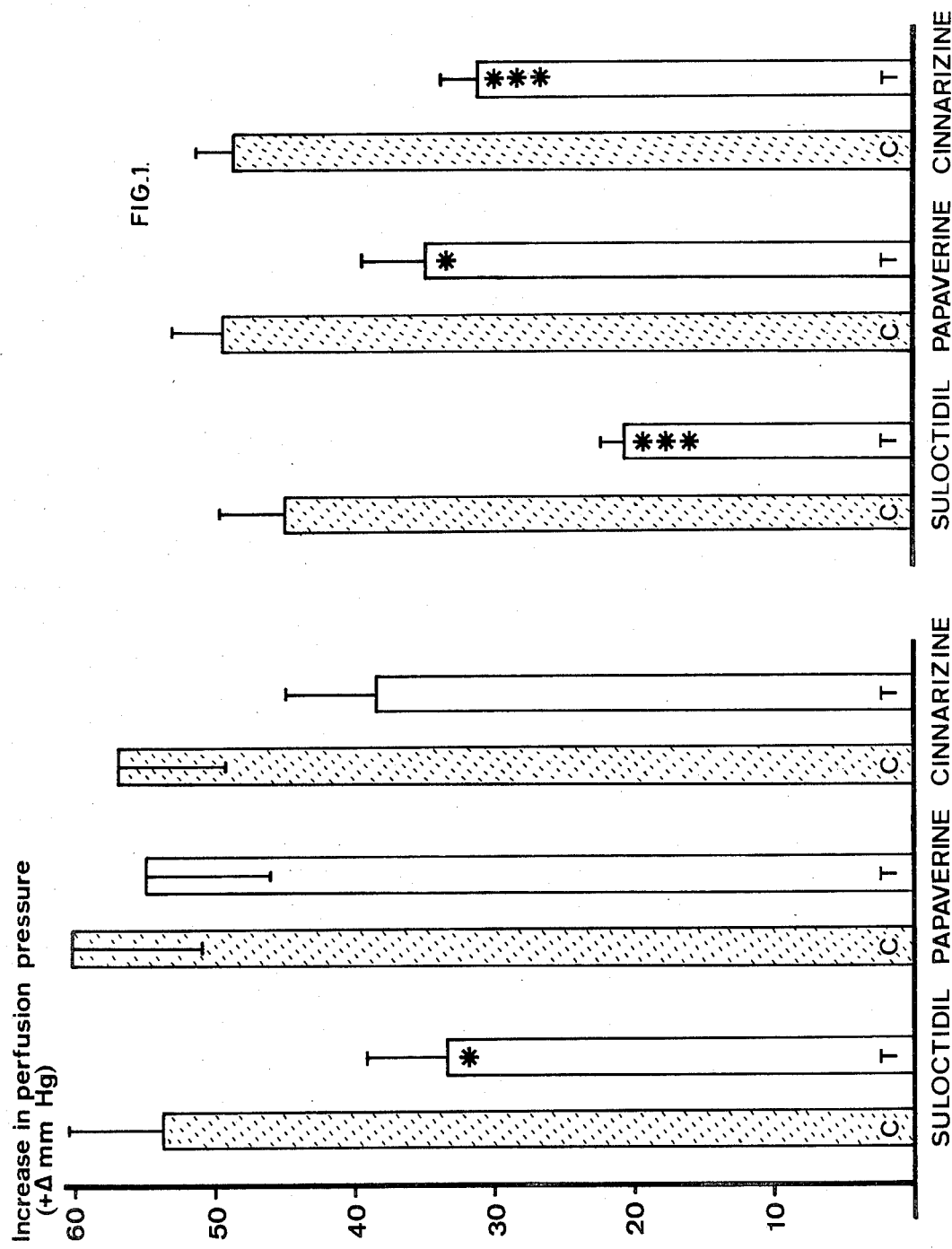

United States Patent [19]

Lambelin et al.

[11] 4,228,187
[45] Oct. 14, 1980

[54] ALKYL AND CYCLOALKYLTHIOPHENYLALKYLAMINOALKANOLS, THEIR SALTS AND THE PREPARATION THEREOF

[75] Inventors: Georges E. Lambelin; Claude L. Gillet, both of Brussels; Joseph L. Roba, Wanlin, all of Belgium

[73] Assignee: Continental Pharma, Brussels, Belgium

[21] Appl. No.: 718,534

[22] Filed: Aug. 30, 1976

Related U.S. Application Data

[63] Continuation-in-part of Ser. No. 366,508, Jun. 4, 1973, abandoned.

[30] Foreign Application Priority Data

Apr. 9, 1973 [GB] United Kingdom ............... 17001/73

[51] Int. Cl.$^2$ ..................... A61K 31/135; C07C 91/06
[52] U.S. Cl. .................................. 424/330; 260/570.6
[58] Field of Search ....................... 424/330; 260/570.6

[56] References Cited

FOREIGN PATENT DOCUMENTS 2047028 4/1971 Fed. Rep. of Germany ........... 424/330

*Primary Examiner*—Frederick E. Waddell
*Attorney, Agent, or Firm*—Stevens, Davis, Miller & Mosher

[57] ABSTRACT

Amino-alcohols of the formula

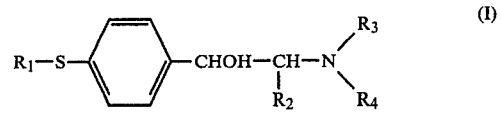

wherein $R_1$ represents either a linear or branched chain alkyl radical having 1 to 4 carbon atoms, or a cycloalkyl radical having 5 or 6 carbon atoms; $R_2$ represents a lower alkyl radical having 1 or 2 carbon atoms; $R_3$ represents a linear or branched chain alkyl radical having 3 to 10 carbon atoms which radical is optionally substituted by phenyl; $R_4$ represents hydrogen, or, together with $R_3$ and the adjacent nitrogen atom, a heterocyclic nucleus of the piperidine type and the corresponding non-toxic salts of said amino-alcohols; preparation of the above and their use as antispasmodic, peripheral vasodilatory and anti-hypertensive agents and as an agent having a protective activity against anoxia of the myocardium.

3 Claims, 2 Drawing Figures

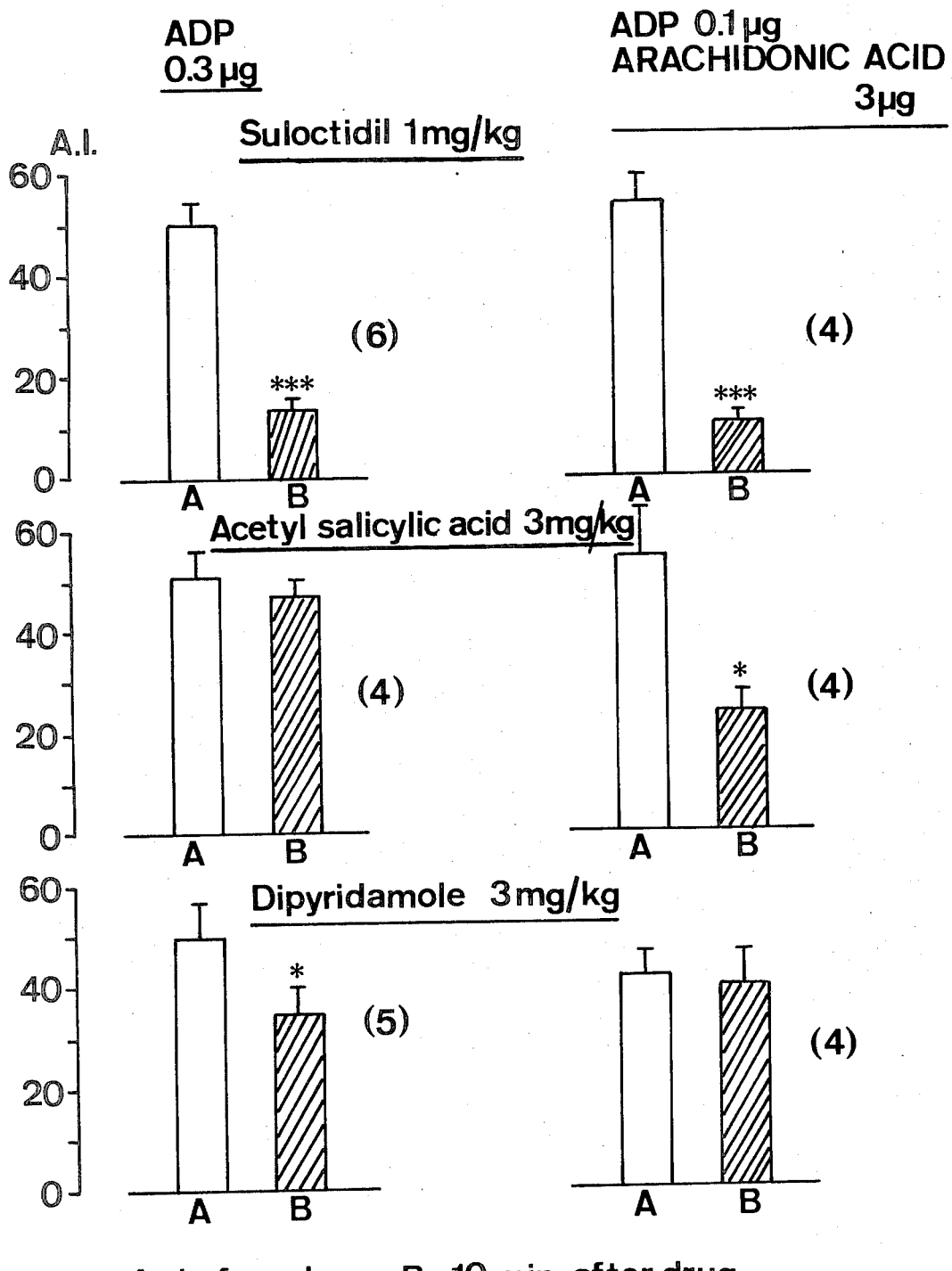

ALKYL AND CYCLOALKYLTHIOPHENYLALKYLAMINOALKANOLS, THEIR SALTS AND THE PREPARATION THEREOF

This application is a continuation-in-part application of U.S. Ser. No. 366,508 filed June 4, 1973, now abandoned.

This invention relates to alkyl and cycloalkylthiophenylalkylaminoalkanols, to the salts of these latter by addition of organic or inorganic acids, and also to the preparation of these compounds.

The present invention provides an amino-alcohol having the formula:

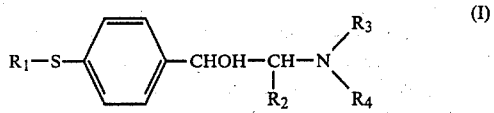

wherein $R_1$ represents either a linear or branched chain alkyl radical having 1 to 4 carbon atoms, or a cycloalkyl radical having 5 or 6 carbon atoms; $R_2$ represents a lower alkyl radical having 1 or 2 carbon atoms; $R_3$ represents a linear or branched chain alkyl radical having 3 to 10 carbon atoms which radical is optionally substituted by phenyl; $R_4$ represents hydrogen, or, together with $R_3$ and the adjacent nitrogen atom a heterocyclic nucleus of the piperidine type.

The invention also includes the non-toxic salts of these compounds, in particular inorganic acid salts such as the hydrochlorides, hydrobromides, phosphates, or sulphates, or organic acid salts such as oxalates, lactates, tartrates, acetates, citrates and moleates.

Among the amino-alcohols corresponding to formula I, in particular the following compounds, a number have important pharmacological properties:
1-(4-isopropylthiophenyl)-2-n-octylaminopropanol
1-(4-methylthiophenyl)-2-n-octylaminopropanol
1-(4-methylthiophenyl)-2-n-octylaminobutanol
1-(4-isobutylthiophenyl)-2-n-octylaminopropanol
1-(4-cyclopentylthiophenyl)-2-n-octylaminopropanol
1-(4-cyclohexylthiophenyl)-2-n-octylaminopropanol Since the most active products of the invention have two centres of asymmetry, it is possible to obtain two racemates corresponding respectively to the erythro and threo configurations, these two racemates can be resolved by conventional methods, for example by the formation of diastereoisomers by the action of optically active acids, such as tartaric, diacetyltartaric, tartranilic, dibenzoyltartaric, or ditolyuoyltartaric acids, and separation of the mixture of diastereoisomers by crystallisation, distillation, chromatography and then liberation of optically active bases from the separated salts.

The same methods may be used if the compounds contain more than two asymmetry centres.

The most active compounds of the invention may therefore be utilised either in the form of a racemic mixture of erythro and threo configurations, or as a mixture of these two forms, or even as the optically active compounds of each of these two forms.

The products of the present invention have antispasmodic, peripheral vasodilatory and antihypertensive activities and exhibit a protective activity against anoxia of the myocardium.

More particularly, it has been found that 1-(4-isopropylthiophenyl)-2-n-octylaminopropanol, mentioned hereinabove, is endowed with several interesting biological properties which can be considered as favourable for the treatment of cerebral and peripheral vascular insufficiencies related to arterisclerosis and its complications.

Said compound is indeed endowed with a potent vascular antispasmodic activity and vasodilating action. It has been observed, after i.v. or oral administration to mice or dogs, inducing an increase in blood flow in both peripheral and cerebral circulations. This effect is related to the antispasmodic activity displayed by 1-(4-isopropylthiophenyl)-2-n-octylaminopropanol on vascular contractile cell. Indeed, said compound inhibits, in vitro and in vivo, vasocontrictions induced by various agents like calcium, norepinephrine, 5-hydroxytryptamine and angiotensine.

Said compound is moreover endowed with a potent antilipolytic activity demonstrated in vitro on catecholamines and methylxanthine induced lipolysis in rat epididymal fat. The compound also displays a direct inhibitory effect on the activity of different lipoprotein-lipases. Moreover, 1-(4-isopropylthiophenyl)-2-n-octylaminopropanol appears in vitro, to be a strong inhibitor of cholesterol biosynthesis. Its inhibitory effect seems more specific than that of standard compounds like clofibrate since the inhibition is maintained when mevalonic acid is used as precursor. This activity of the compound may explain the hypocholesterolemic and "normolipoproteinemic" effects observed in vivo in experimental type II hyperlipidemia in monkeys.

Two additional properties of 1-(4-isopropylthiophenyl-2-n-octylaminopropanol deal with hematological factors: blood viscosity and platelet functions. In pilot studies, conducted in geriatric patients, it appears that long-term treatment with this compound at therapeutic dosage regimen is able to reduce by about 10% the blood hyperviscosity observed before the treatment. This blood-viscosity lowering effect seems to be accompanied by a parallel reduction of the plasma fibrinogen levels.

Finally 1-(4-isopropylthiophenyl)-2-n-octylaminopropanol is endowed with potent platelet antiaggregating properties observed in vitro and in vivo, in both.

The active compounds of the invention may be administered in association with various pharmaceutical excipients, either orally or parenterally.

For oral administration, dragees, granules, tablets, capsules, solutions, syrups, emulsions or suspension are used containing an active compound(s) and also containing the conventional additives or excipients of Gelenic pharmacy. For parenteral administration, the active compound is used with a liquid, such as sterile water, or with an oil, such as peanut oil or ethyl oleate.

These active compounds may be used alone or in combination with other active products having a similar or different activity or activities.

The novel compounds according to the invention are prepared in accordance with the general method defined as follows:

The amino-alcohols according to formula I and their salts are prepared from a compound having formula II:

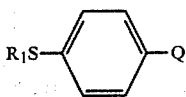

(II)

or possibly, according to the meaning of Q, from a salt of a compound corresponding to this formula, in which $R_1$ has the meaning given above and Q represents one of the following groups

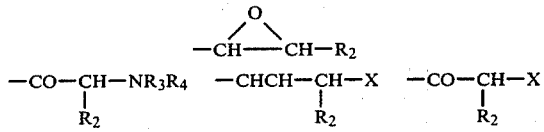

(in these groups $R_2$, $R_3$ and $R_4$ have the meaning given previously), wherein X represents a halogen atom.

This general method may be carried out in either of two modes which are essentially determined by the starting product, that is to say by the meaning of Q in formula II.

Method A

In accordance with the first mode an α-amino ketone corresponding to formula II is reduced in which Q represents a group

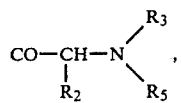

$R_2$ and $R_3$ having the meaning given previously, $R_5$ is the same as $R_4$ or is a protective group which can be eliminated subsequently by hydrolysis or hydrogenolysis, such as a benzyl, trityl, acetyl, formyl or benzohydryl group.

This reduction may be effected in the usual manner, for example most easily by the action of alkali metal hydrides, such as sodium borohydride, in a solvent such as methanol or ethanol (preferably at low temperature), or by using aluminium and lithium hydrides in a solvent, such as diethyl ether or tetrahydrofuran, or again by the action of an aluminium alcoholate, such as aluminium isopropylate in a solvent such as isopropanol, most advantageously at the reflux temperature of isopropanol. The reduction may also be effected by hydrogenation in the presence of a catalyst, such as palladium on carbon, Raney nickel, or platinum oxide in a solvent such as methanol, ethanol, or dioxane.

As indicated above the most important products of this invention can have two erythro and threo configurations. The choice of the starting amino ketone and the conditions of reduction make it possible to obtain one or the other of these two forms stereoselectively. Thus, the reduction of an amino ketone or

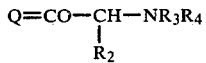

and in which $R_4$=hydrogen leads, in the general conditions described above, to an amino alcohol of erythro configuration.

In order to obtain a compound of threo configuration the reduction is carried out on an amino ketone, where

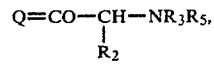

in which $R_1$ and $R_3$ are as defined above and $R_5$ is a protective group which can be eliminated subsequently by hydrolysis or hydrogenolysis, such as a benzyl, trityl, acetyl, formyl or benzohydryl group; this reduction is preferably effected in this case by the action of an alkali metal hydride, such as sodium borohydride or aluminium and lithium hydride.

The starting amino ketones are easily obtainable, for example by the action of an amine $R_3R_4NH$ on an α-halo ketone in solvents, such as ether, benzene, chloroform, dioxane, methanol, isopropanol or acetonitrile.

It is well known in the literature, however, that a reaction of this type generally gives low yields, this being due to the formation of numerous secondary products and to the instability of the α-amino ketones. The applicants have perfected a method of synthesis which makes it possible to obtain amino alcohols of the general structure I in excellent yields, and this preferably by not isolating the intermediate amino ketone; the preferred solvents for this type of reaction are alcohols, such as methanol, ethanol or isopropanol.

Method B

In accordance with this mode of preparation, a compound having the general formula II in which Q represents a group

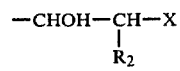

is reacted with an amine of the type $R_3R_4NH$. $R_2$, $R_3$, $R_4$, and X having the meaning given previously.

This reaction is effected in a solvent, such as an alcohol, chloroform, dioxane, carbon tetrachloride, and most readily in the presence of a product fixing the halogenated hydracid formed, such as a tertiary organic or a mineral base, or, alternatively, in the presence of an excess of an amine. In this reaction the group

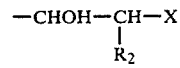

first gives an oxirane of the type

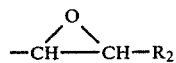

which then reacts with the amino compound.

This method therefore comprises the preparation of the desired amino alcohols from oxiranes as starting materials.

The amino-alcohol salts may be formed, according to the invention and as indicated previously, by the general method described above. This method has several variants.

In general, the salts may be formed using well known variations of the above metioned general process, such as the reaction in equimolecular quantities of an amino alcohol with an acid in a suitable solvent such as an alcohol followed by precipitation of the salt by the addition of another solvent which is miscible with the first solvent and in which the salt is insoluble, for example ether; or by the neutralisation of an ethereal solution of the acid or of the base by the base or acid. The acids used are either inorganic acids or organic acids. As suitable inorganic acids there are preferably used hydrochloric acid, hydrobromic acid, sulphuric acid, phosphoric acid or perchloric acid. The organic acids are either carboxylic acids or sulphonic acids such as formic, acetic, propionic, glycollic, lactic, citric, ascorbic, fumaric, maleic, pamoic, succinic, tartaric, phenylacetic, benzoic, p-aminobenzoic, anthranilic, p-hydrobenzoic, salicylic, methanesulphonic or ethanedisulphonic acid.

The invention will now be further described and illustrated by way of the following Examples, these Examples being followed by Table I which lists the characteristics of an important group of compounds prepared in accordance with the present invention.

Tables II to VI group pharmaceutical results and FIGS. 1 and 2 annexed give a graphic representation of some of said results in comparison to standard agents.

EXAMPLE 1

1-(4-isopropylthiophenyl)-2-n-octylaminopropanol 57 g of α-bromo-4-isopropylthiopropiophenone (0,2 M), 26 g of n-octylamine (0,2 M) and 300 ml of methanol are brought to reflux for 3 hrs. The solution is cooled to about 0° C. and while stirring there is added a solution of 8 g of $NaBH_4$ in 100 ml of water. Stirring is carried further overnight at room temperature and the methanol is evaporated. The residue is diluted with 200 ml of water and extracted with methylene chloride. The organic phase is dried on $MgSO_4$, the residue is evaporated recrystallized in n-pentane or in a methanol-water mixture. 40.2 g are obtained. Yield: 60%.

MP (°C): 62-63 and 232-234 for the hydrochloride (Melting Point)

|  |  | C | H | N |
|---|---|---|---|---|
| Percentage analysis | % calc. | 71.46 | 10.45 | 4.15 |
|  | % found | 71.40 | 10.30 | 4.40 |

The erythro configuration of the product is demonstrated by studying the nuclear magnetic resonance spectrum.

EXAMPLE 2

1-(4-isopropylthiophenyl)-2-n-octylaminopropanol (a) To 28.7 g of α-bromo-4-isopropylthiopropiophenone (0,1 M) in 100 ml of isopropanol there are rapidly added 14.2 g of n-octylamine while stirring, and then the mixture is brought to 80° C. for 1 hr. The solvent is evaporated under vacuum, the residue is diluted with 1 l. of ether and it is left to stand overnight in the refrigerator. The precipitate obtained is filtered and dried. There are thus obtained 25 g of α-n-octylamino-4-isopropylthiopropiophenone hydrobromide. Yield: 60%-MP (°C.): 162°-164°.

|  |  | C | H | N |
|---|---|---|---|---|
| percentage analysis: | % calc. | 57.70 | 8.25 | 3.35 |
|  | % found | 57.85 | 8.05 | 3.10 |

The reaction may likewise be carried out in acetonitrile and methanol.

(b) 41.6 g of preceding product (0,1 M) in 200 ml of methanol are cooled in an ice bath to 0° C. There is added drop by drop while stirring a solution of 4.1 g of $NaBH_4$ in 50 ml of water and 2 ml of 5% NaOH, then stirring takes place for 2 hrs. at room temperature. The methanol is evaporated under vacuum, it is diluted with 200 ml of water, it is extracted with methylene chloride or ether, the organic phase is dried on $MgSO_4$ and the solvent is evaporated under vacuum. The oily residue obtained solidifies rapidly and is recrystallized in pentane. 33.2 g are thus obtained. Yield: 90%-MP (°C.): 62-63.

EXAMPLE 3

1-(4-methylthiophenyl)-2-n-octylaminopropanol

To 52 g of α-bromo-4-methylthiopropiophenone (0,2 M) in 200 ml of ethanol there are rapidly added while stirring 26 g of n-octylamine (0,2 M) and refluxed for 4 hrs. The mixture is cooled to 0° C. and 8 g of $NaBH_4$ are gradually added, the temperature being maintained between 0° and 5° C. Stirring is effected overnight at room temperature and the solvent is evaporated under vacuum. The residue is diluted with 200 ml of water, acidified with 20% HCl, washed twice with 100 ml of ether, alkalized with 20% NaOH and extracted with ether. The organic phase is dried on $MgSO_4$ and filtered. A stream of dry gaseous hydrochloric acid is passed through the ethereal solution and the precipitate obtained is filtered. This latter is recrystallized in a mixture of acetone and methanol. 43 g of 1-(4-methylthiophenyl)-2-n-octylaminopropanol hydrochloride are obtained. Yield: 62%-MP (°C.): 231-232.

|  |  | C | H | N |
|---|---|---|---|---|
| Elementary analysis | % calc. | 62.49 | 9.32 | 4.05 |
|  | % found | 62.70 | 9.40 | 3.95 |

EXAMPLE 4

1-(4-isopropylthiophenyl)-2-n-octylaminopropanol 29 g of α-bromo-4-isopropylthiopropiophenone (0,1 M), 43.8 g of benzyloctylamine (0,2 M) and 300 ml anhydrous acetonitrile are stirred for 20 hrs. at room temperature. The precipitate is filtered and the organic phase is evaporated. The oily residue obtained is taken up by 200 ml of anhydrous ether and there is added drop by drop a solution of 4 g of $H_4LiAl$ in 150 ml of anhydrous ether. The mixture is refluxed for two hours and the excess hydride is destroyed by the addition of 4 ml of water. The organic phase is filtered by passing a dry gaseous stream of hydrochloric acid there is obtained 38 g of 1-(4-isopropylthiophenyl)-2-benzyloctylaminopropanol.

MP (0° C.): 104-105

|  |  | C | H | N |
|---|---|---|---|---|
| percentage analysis | % calc. | 69.86 | 9.12 | 3.02 |

-continued

|  |  | C | H | N |
|---|---|---|---|---|
|  | % found | 69.64 | 8.92 | 2.87 |

10 g of the preceding product, 100 ml of ethanol, 1 g of palladium on 10% carbon and 1 ml of concentrated HCl are hydrogenated at room temperature and normal pressure.

The solution is filtered and it is evaporated under vacuum. After recrystallization in methanol ether there are thus obtained: 7.8 g of 4-(isopropylthiophenyl)-2-n-octylaminopropanol hydrochloride.

MP (0° C.): 222-224 (with decomposition)

|  |  | C | H | N |
|---|---|---|---|---|
| percentage analysis | % calc. | 64.22 | 9.70 | 3.74 |
|  | % found | 64.20 | 9.50 | 3.60 |

The threo configuration of the product is demonstrated by studying the nuclear magnetic resonance spectrum.

EXAMPLE 5

1-(4-isopropylthiophenyl)-2-n-octylaminopropanol (a) To 15 g of α-bromo-4-isopropylthiopropiophenone in 200 ml of methanol cooled to 0° C. there are gradually added while stirring 4.5 g of $NaBH_4$. Stirring is effected for 30 minutes at room temperature and then it is diluted with 200 ml of water and acidified with 45% HBr. Extraction with ether is effected and the organic phase is dried on $MgSO_4$ and evaporated. 15.6 g of an oil are obtained, the homogeneity of which is verified by CCM and which is used in the following operation.

(b) 15 g of the preceding product, 75 ml of n-octylamine and 100 ml of absolute ether are brought to reflux for 20 hrs. The solvent and excess amine are evaporated under vacuum. The residue is treated with 200 ml of 5% HCl, the precipitate is filtered and washed with water and with diisopropylether. Recrystallization is effected in acetone and there are thus obtained 10 g of 1-(4-isopropylthiophenyl)-2-n-octylaminopropanol hydrochloride.

Yields: 51% (stages a and b) MP: 222-224 (with decomposition). The free base is recrystallized in pentane.

MP (°C.): 51-52.

|  |  | C | H | N |
|---|---|---|---|---|
| percentage analysis | % calc. | 71.46 | 10.45 | 4.15 |
|  | % found | 71.50 | 10.45 | 4.30 |

The threo configuration of the product is demonstrated by studying the nuclear magnetic resonance spectrum.

TABLE I $R_1S-\text{C}_6\text{H}_4-CHOH-CH(R_2)-N-R_3R_4$

| No | $R_1$ | $R_2$ | $-N-R_3R_4$ | MP(°C.)[1] |  |
|---|---|---|---|---|---|
| 1 | isoC$_3$H$_7$ | CH$_3$ | —NHnC$_4$H$_9$ | 221-222 | (CH$_3$OH) |
| 2 | isoC$_3$H$_7$ | CH$_3$ | —NHnC$_8$H$_{17}$ | 60-62[2] | (n-pentane) |
| 3 | isoC$_3$H$_7$ | CH$_3$ | —NHisoC$_3$H$_7$ | 195-196 | (CH$_3$OH-ether) |
| 4 | isoC$_3$H$_7$ | CH$_3$ | —NHsecC$_4$H$_9$ | 171,5-173 | (CH$_3$OH-ether) |
| 5 | isoC$_3$H$_7$ | CH$_3$ | —NHtC$_4$H$_9$ | 173-175 | (CH$_3$OH-ether) |
| 6 | isoC$_3$H$_7$ | C$_2$H$_5$ | —NHnC$_4$H$_9$ | 195-196,5 | (CH$_3$OH-ether) |
| 7 | isoC$_3$H$_7$ | C$_2$H$_5$ | —NHisoC$_3$H$_7$ | 172-173 | (CH$_3$OH-ether) |
| 8 | isoC$_3$H$_7$ | C$_2$H$_5$ | —NHnC$_8$H$_{17}$ | 198-200 | (isoC$_3$H$_7$OH) |
| 9 | isoC$_3$H$_7$ | C$_2$H$_5$ | —NHsecC$_4$H$_9$ | 151-152,5 | (CH$_3$OH-ether) |
| 10 | CH$_3$ | CH$_3$ | —NHnC$_4$H$_9$ | 225-227 | (CH$_3$OH-acetone) |
| 11 | CH$_3$ | CH$_3$ | —NHnC$_8$H$_{17}$ | 231-232 | (CH$_3$OH-acetone) |
| 12 | C$_2$H$_5$ | CH$_3$ | —NHnC$_4$H$_9$ | 216-217 | (CH$_3$OH-acetone) |
| 13 | C$_2$H$_5$ | CH$_3$ | —NHnC$_8$H$_{17}$ | 230-232 | (CH$_3$OH-acetone) |
| 14 | C$_6$H$_{11}$ | CH$_3$ | —NHnC$_4$H$_9$ | 207-209 | (CH$_3$OH-ether) |
| 15 | C$_6$H$_{11}$ | CH$_3$ | —NHnC$_8$H$_{17}$ | 212-215 | (CH$_3$OH-ether) |
| 16 | C$_6$H$_{11}$ | CH$_3$ | —NHsecC$_4$H$_9$ | 189-191 | (CH$_3$OH-ether) |
| 17 | CH$_3$ | C$_2$H$_5$ | —NHnC$_4$H$_9$ | 198-200 | (CH$_3$OH-acetone) |
| 18 | CH$_3$ | C$_2$H$_5$ | —NHnC$_8$H$_{17}$ | 175-178 | (CH$_3$OH-acetone) |
| 19 | C$_2$H$_5$ | C$_2$H$_5$ | —NHnC$_4$H$_9$ | 193-195 | (CH$_3$OH-acetone) |
| 20 | C$_2$H$_5$ | C$_2$H$_5$ | —NHnC$_8$H$_{17}$ | 180-183 | (CH$_3$OH-acetone) |
| 21 | C$_6$H$_{11}$ | CH$_3$ | —NHtC$_4$H$_9$ | 209-210 | (CH$_3$OH-ether) |
| 22 | isoC$_4$H$_9$ | CH$_3$ | —NHisoC$_3$H$_7$ | 186-187 | (CH$_3$OH-acetone) |
| 23 | isoC$_4$H$_9$ | CH$_3$ | —NHsecC$_4$H$_9$ | 181-183 | (CH$_3$OH-acetone) |
| 24 | isoC$_4$H$_9$ | CH$_3$ | NHtC$_4$H$_9$ | 183-184 | (CH$_3$OH-ether) |

TABLE I-continued $$R_1S-\text{C}_6H_4-CHOH-CH(R_2)-N-R_3R_4$$

| No | R₁ | R₂ | —N—R₃R₄ | MP(°C.)[1] | |
|---|---|---|---|---|---|
| 25 | isoC₄H₉ | CH₃ | NHnC₄H₉ | 73–75[2] | (C₆H₆-petroleum ether) |
| 26 | isoC₄H₉ | CH₃ | —NHnC₈H₁₇ | 70–72[2] | (n-hexane) |
| 27 | cyclohexyl | C₂H₅ | —NHisoC₃H₇ | 192–194 | (CHCl₃-petroleum ether) |
| 28 | isoC₃H₇ | CH₃ | —NHnC₆H₁₃ | 67–68[2] | (n-pentane) |
| 29 | isoC₃H₇ | CH₃ | —NHnC₇H₁₅ | 68–69[2] | (n-pentane) |
| 30 | isoC₃H₇ | CH₃ | —NHnC₉H₁₉ | 52–53[2] | (n-pentane) |
| 31 | isoC₃H₇ | CH₃ | —NHnC₁₀H₂₁ | 55–56[2] | (n-pentane) |
| 32 | cyclopentyl | CH₃ | —NHnC₈H₁₇ | 64–65[2] | (CH₃OH—H₂O) |
| 33 | cyclohexyl | CH₃ | —N(piperidine) | 70–71,5[2] | (n-hexane) |
| 34 | cyclohexyl | C₂H₅ | —N(piperidine) | 219–221 | (CH₃OH-ether) |
| 35 | isoC₃H₇ | CH₃ | —NH—CH(CH₃)—CH₂—C₆H₅ | 108–109[2] | (n-hexane) |

[1] the recrystallization solvent is given in brackets; the melting point shown is that of the hydrochloride, unless indicated to the contrary.
[2] melting point of the free base.

Table II given below groups the pharmacological results of the compounds in Table I. The numbers in the first column of this Table II correspond to the compounds having the same number in Table I.

TABLE II

| No (1) | DL₅₀ mouse p.o.mg/kg | Peripheral vasodilatory activity (2) | Anti-hypertensive activity (3) | Antispasmodic activity CE₁₀₀ (μ g γ 60 ml) Hist. | Ac.chol. | BaCl₂ | β-lytic activity (4) | Protective activity against anoxia (5) |
|---|---|---|---|---|---|---|---|---|
| 1 | 680 (495–935) | ++ | | 500 | 1000 | 500 | + | 0 |
| 2 | 3700 (3008–4551) | ++++ | 0 | 100 | 100 | 100 | + | 0 |
| 3 | 630 (450–882) | ++ | | 1000 | 1000 | >1000 | ++ | 0 |
| 4 | 520 (416–650) | ++ | | 1000 | 1000 | 500 | + | 0 |
| 5 | | + | | >1000 | 1000 | 1000 | +++ | 0 |
| 6 | >1000 | ++ | | 500 | 100 | 1000 | +++ | 0 |
| 7 | | ++ | | 1000 | 200 | 1000 | ++ | 0 |
| 8 | >4000 | ++++ | 0 | 500 | 500 | 100 | 0 | 0 |
| 9 | | ++ | | 1000 | 200 | 500 | 0 | ++ |
| 10 | ±100 | ++ | 0 | 1000 | 500 | 1000 | ++ | + |
| 11 | 970 (693–1358) | ++++ | ++ | 200 | 200 | 100 | | 0 |
| 12 | 312 (215–425) | ++ | | 1000 | 500 | 1000 | | 0 |
| 13 | 1750 (1306–2345) | | ++ | 100 | 200 | 100 | 0 | 0 |
| 14 | | +++ | | 500 | 100 | 200 | | |
| 15 | ±5000 | | ++ | 1000 | 500 | 1000 | | |
| 16 | | | | 500 | 200 | 200 | | |
| 17 | 122 (86–173) | ++ | + | 1000 | 1000 | 1000 | | 0 |
| 18 | ±3500 | ++++ | 0 | 200 | 200 | 500 | | 0 |
| 19 | 640 (400–1024) | ++ | | 1000 | 1000 | 500 | | 0 |
| 20 | ±2450 | | 0 | 200 | 100 | 100 | | |
| 21 | | ++ | 0 | 500 | 100 | 500 | | |
| 22 | 1280 (948–1728) | ++ | | 500 | 1000 | 500 | | 0 |
| 23 | | ++ | | 200 | 200 | 500 | | 0 |
| 24 | | ++ | | 200 | 1000 | 500 | | |
| 25 | 1350 (1125–1620) | +++ | | 200 | 100 | 200 | | 0 |
| 26 | >4000 | ++++ | | 200 | 200 | 200 | | 0 |
| 27 | | | | 500 | 200 | 200 | | |

TABLE II-continued

| No (1) | DL$_{50}$ mouse p.o.mg/kg | Peripheral vasodilatory activity (2) | Anti-hypertensive activity (3) | Antispasmodic activity CE$_{100}$ ($\mu$ g $\gamma$ 60 ml!) Hist. | Ac.chol. | BaCl$_2$ | $\beta$-lytic activity (4) | Protective activity against anoxia (5) |
|---|---|---|---|---|---|---|---|---|
| 28 | 1450 (1094–1921) | | | | | | | |
| 29 | ±2400 | | | | | | | |
| 30 | | | | | | | | |
| 31 | | | | | | | | |
| 32 | >4000 | | ++ | | | | | |
| 33 | | ++++ | | >1000 | >1000 | >1000 | | |
| 34 | | ++ | | 1000 | 100 | 200 | | |
| 35 | 2100 (1500–2940) | ++++ | ± | 200 | 500 | 500 | | |

(1) the limits of reliability (p : 0.95) are given in brackets.
(2) perfused dog's paw
(3) spontaneously hypertensive rat; 15 mg/kg per os;
   ± reduction of systolic pressure up to 10 mm of Hg
   + reduction of systolic pressure of 10 to 20 mm Hg
   ++ reduction of systolic pressure of at least 20 mm of Hg
(4) guinea pig atria's; antagonism of the positive chronotropic effect of noradrenaline
(5) guinea pig atria's;
   ++ = increase in survival time of more than 25%
   + = increase in survival time of 10 to 20%

As already indicated above the compounds corresponding to formula 1 may be administered in association with various pharmaceutical excipients, that is orally or parenterally.

There are given in the following, in this respect, some non-restrictive examples of galenic formulations which contain as active product 1-(4-isopropylthiophenyl)-2-n-octylaminopropanol.

| Injection i.m. | |
|---|---|
| 1-(4-isopropylthiophenyl)-2-n-octylaminopropanol | 100 mg |
| Isopropyl myristate | 0.75 ml |
| Peanut oil qs ad | 3 ml |
| 1-(4-isopropylthiophenyl)-2-n-octylaminopropanol | 50 mg |
| Ethyl alcohol | 0.50 ml |
| Polyethylene glycol 400 | 0.25 ml |
| Propylene glycol | 0.50 ml |
| 10% acetic acid | 0.125 ml |
| 70% sorbitol | 0.75 ml |
| Distilled water qs ad | 3 ml |

| Solution for oral administration | |
|---|---|
| 1-(4-isopropylthiophenyl)-2-n-octylaminopropanol | 5 mg |
| Ethyl alcohol | 0.1 ml |
| Propylene glycol | 0.05 ml |
| 10% acetic acid | 0.05 ml |
| Plain syrup (saccharose 65%) qs ad | 1 ml |
| 1-(4-isopropylthiophenyl)-2-n-octylaminopropanol | 5 mg |
| Ethyl alcohol | 0.2 ml |
| 10% acetic acid | 0.04 ml |
| Plain Syrup qs ad | 1 ml |
| 1-(4-isopropylthiophenyl)-2-n-octylaminopropanol | 10 mg |
| Ethyl alcohol | 0.25 ml |
| 10% acetic acid | 0.04 ml |
| Plain syrup qs ad | 1 ml |

| Compressed tablets. | |
|---|---|
| 1-(4-isopropylthiophenyl)-2-n-octylaminopropanol | 50 mg |
| Lactose | 20 mg |
| Aerosil | 2 mg |
| Starch STA-RX 1500 | 18 mg |
| Calcium phosphate (CaHPO$_4$) | 25 mg |
| Microcrystalline cellulose | 100 mg |
| Sodium acetate | 15 mg |
| 1-(4-isopropylthiophenyl)-2-n-octylaminopropanol | 50 mg |
| Microcrystalline cellulose | 80 mg |
| Sodium acetate | 25 mg |
| Auby-gel X 52 | 20 mg |

| Compressed tablets. | |
|---|---|
| Maize starch | 50 mg |
| 1-(4-isopropylthiophenyl)-2-n-octylaminopropanol | 50 mg |
| Microcrystalline cellulose | 100 mg |
| Starch STA-RX 1500 | 99 mg |
| Aerosil | 1 mg |
| 1-(4-isopropylthiophenyl)-2-n-octylaminopropanol | 50 mg |
| Maize starch | 50 mg |
| Sodium acetate | 15 mg |
| Magnesium stearate | 2 mg |
| Aerosil | 3 mg |
| Starch STA-RX 1500 | 80 mg |

| Capsules. | |
|---|---|
| 1-(4-isopropylthiophenyl)-2-n-octylaminopropanol | 50 mg |
| Starch STA-RX 1500 | 94 mg |
| Magnesium stearate | 1 mg |
| Sodium laurylsulphate | 5 mg |
| 1-(4-isopropylthiophenyl)-2-n-octylaminopropanol | 50 mg |
| Microcrystalline cellulose | 70 mg |
| Maize Starch | 30 mg |
| Peanut oil | 0.01 mg |
| Sodium laurylsulphate | 5 mg |
| 1-(4-isopropylthiophenyl)-2-octylaminopropanol | 50 mg |
| Sodium laurylsulphate | 5 mg |
| Microcrystalline cellulose | 70 mg |
| Magnesium oxide | 20 mg |
| 1-(4-isopropylthiophenyl)-2-n-octylaminopropanol | 50 mg |
| Starch STA-RX 1500 | 100 mg |
| Magnesium stearate | 1 mg |
| Sodium laurylsulphate | 10 mg |
| Microcrystalline cellulose | 30 mg |
| Aerosil | 1 mg |

It has been ascertained that the 1-(4-isopropylthiophenyl)-2-n-octylaminopropanol (suloctidil) has a greater degree of activity than papaverine, a standard agent of clinical use as regards peripheral vasodilatatory activity, particularly considering its duration of action.

These findings are based on table III which follows:

TABLE III

| Product and Dosage (1) | | Amplitude (2) | Half-life (3) | Duration of effect (4) |
|---|---|---|---|---|
| | 10 | 42 | 94 | 226 |
| suloctidil | 20 | 59 | 139 | 299 |
| | 30 | 67 | 158 | 390 |
| papa- | 10 | 40 | 19 | 43 |

TABLE III-continued

| Product and Dosage (1) | Amplitude (2) | Half-life (3) | Duration of effect (4) |
|---|---|---|---|
| veri- | 20 | 51 | 25 | 45 |
| ne | 30 | 54 | 26 | 47 |

(1) intra-arterial injection in dog (5 animals) 10, 20 and 30 μg/kg.
(2) maximum vasodilatory effect in mm of Hg.
(3) and (4) expressed in seconds.

Said compound appears to be in vivo a potent inhibitor of vasoconstrictions induced, for example, by norepinephrine and agiotensine in the femoral circulation of dogs. It is more active than standard agents like papaverine and cinnarizine.

FIG. 1 is a graphic representation of the antispasmodic activity of suloctidil, cinnarizine and papaverine on the femoral circulation.

The vasoconstrictions are induced by i.a. norepinephrine (n=10) or angiotensine (n=8) during solvent (C) or drug (T) infusion. Suloctidil, cinnarizine and papaverine are administrated i.a. at equal dose, 10 μg/kg/min.

Vertical bars are standard errors of the means and * or *** indicate statistically significant differences from the corresponding control values at the thresholds $\alpha=0.05$ and 0.001 respectively.

It has also been found that 1-(4-isopropylthiophenyl)-2-n-octylaminopropanol (suloctidil) markedly inhibits the biosynthesis of cholesterol, and that this activity is qualitatively different from that of a standard agent like clofibrate.

This is shown by the data given in table IV which is as follows:

Table IV

Inhibition of cholesterol biosynthesis in vitro (rat liver). Inhibitory effect of suloctidil and clofibrate on the incorporation of 1-$^{14}$C-acetate (AA) and 2-$^{14}$C-mevalonate (MVA). Results are mean values and range, expressed in % of inhibition. Unless otherwise stated, n = 3.

| Concentration (M) | Suloctidil | | Clofibrate | |
|---|---|---|---|---|
| | AA | MVA | AA | MVA |
| $5 \cdot 10^{-6}$ | 5 | 4.5 | 0 | 0 |
| | (3–7) | (1–7) | (0–0) | (n = 1) |
| $10^{-5}$ | 27.5 | 9.9 | 4.2 | 0 |
| | (25–30) | (8–12) | (1–7) | (n = 1) |
| $5 \cdot 10^{-5}$ | 43.4 | 15.4 | 20 | 1 |
| | (41–47) | (13–16) | (n = 1) | (n = 1) |
| $10^{-4}$ | 49.4 | 25.9 | 47.4 | 8 |
| | (47–52) | (23–29) | (47–48) | (n = 1) |
| $2 \cdot 10^{-4}$ | — | 43.2 | — | 8 |
| | | (42–44) | | (n = 1) |

As already mentioned hereinabove 1-(4-isopropylthiophenyl)-2-n-octylaminopropanol (suloctidil) is endowed with platelet anti-aggregating properties.

In ex-vivo conditions, single oral administration of 1-(4-isopropylthiophenyl)-2-n-octylaminopropanol (200 mg or more) to healthy volunteers strongly inhibits ADP, L-epinephrine, collagen and Thrombofax induced aggregation. After a single oral intake of 200 mg the effect lasts for at least 6 h. Repeated administration of 1-(4-isopropylthiophenyl)-2-n-octylaminopropanol seems to optimalize its anti-platelet activity. It must be noted that in patients submitted to long-term oral anticoagulants therapy, the simultaneous administration of relatively high daily dosages (900 mg) of 1-(4-isopropyl thiophenyl)-2-n-octylaminopropanol does not markedly decrease prothrombine levels. Other studies show that repeated administration of the drug does not prolong bleeding time in man. Moreover, investigations on its mode of action indicate that the mechanism involved are quantitatively and qualitatively different from these of the other known anti-platelet agents.

FIG. 2 is a graphic representation of the inhibition by suloctidil, acetylsalicyclic acid and dipyridamole of platelet aggregation induced in vivo (rat) by ADP alone or in combination with arachidonic acid.

AI means the aggregation index.

FIGS. in () are number of experiment. * and *** indicate statistically significant difference from predrug values at the thresholds $\alpha=0.05$ and 0.001 respectively.

Since platelet aggregation is considered to be of paramount importance in thrombus formation, this antiplatelet activity of 1-(4-isopropylthiophenyl)-2-n-octylaminopropanol (suloctidil) is likely to explain its anti-thrombotic properties. Oral administration of 1-(4-isopropylthiophenyl-2-n-octylaminopropanol to mice or rats blocked or decreased the formation of platelets emboli triggered by ADP.

At the same dose, 1-(4-isopropylthiophenyl)-2-n-octylaminopropanol (suloctidil) is as active as acetyl salicyclic acid, a well known antiplatelet agent.

In animals, 1-(4-isopropylthiophenyl)-2-n-octylaminopropanol reduces thromboformation in arteries and veins. In the dog, the incidence of occluding thrombosis of the femoral artery enzymatically induced damage to the endothelium is significantly lower in 1-(4-isopropylthiophenyl)-2-n-octrylaminopropanol treated dogs (5 times 5 mg/kg i.m.) than in the controls. Acetylsalicyclic acid (5 times 100 mg/kg p.o.) is also effective in these conditions (see table V given below).

Deep veins thrombosis is also prevented by 1-(4-isopropylthiophenyl)-2-n-octylaminopropanol. In rats fed an hyperlipidemic diet for 3 months, multiple thrombosis of the hepatic veins induced by bacterial endotoxin injection is markedly less frequent and less developped in 1-(4-isopropylthiophenyl)-2-n-octylaminopropanol(-suloctidil) treated animals than in the corresponding controls. (see table VI given below). This protection is still conferred by a 10 mg/kg oral dose of 1-(4-isopropylthiophenyl)-2-n-octylaminopropanol, given in the diet.

TABLE V.

Prevention of arterial thrombosis.

Thrombosis was induced in the femoral artery of anesthetized dogs by a 30 min perfusion, in a catheterized area of the vessel, of a solution of pronase. Drugs administrations were made at 24 h intervals, for 5 days the last dosage being given 30 min before anesthesia.

| Drug | Dose | n | n dogs with occluding thrombosis |
|---|---|---|---|
| — | — | 16 | 10 |
| Suloctidil | 5 × 5 mg/kg i.m. | 16 | 3* |
| Acetylsa-licylic acid | 5 × 100 mg/kg p.o. | 10 | 1* |

*indicates data statistically different from the controls at the threshold $\alpha = 0.05$.
Suloctidil = 1-(4--isopropylthiophenyl)-2-n-octylaminopropanol.

TABLE VI.

Prevention of deep veins thrombosis.

Thrombosis in the hepatic veins were induced in rats fed an hyperlipidemic diet for 3 months by i.v. injection of endotoxin (lipopolysaccharide B from Salmonella typhosa, 1 mg/kg).
Suloctidil was administered into the diet. The importance of the thrombosis was assessed by scoring the subsequent red hepatic infarcts according to their number and surface.

| Groups | I | II | III |
|---|---|---|---|
| Suloctidil | | | |
| Dose : mg/kg/day | 0 | 10 | 25 |
| n rats with | | | |
| score 0 | 13 | 25** | 23** |
| 1 | 12 | 4* | 5* |
| 2 | 1 | 0 | 0 |
| 3 | 2 | 0 | 0 |

* and ** indicate data statistically different from the controls at the thresholds $\alpha$ = 0.05 or 0.01, respectively.

All these properties of 1-(4-isopropylthiophenyl)-2-n-octylaminopropanol, namely vascular antispasmodic effect, normolipoproteinemic activity, blood viscosity lowering action, anti-aggregating and anti-thrombotic activity, converge to make this drug a promising candidate for the long term management of atherisclerosis and its complications.

What we claim is:

1. 1-(4-isopropylthiophenyl)-2-n-octylaminopropanol and its non-toxic salts.

2. 1-(4-isopropylthiophenyl)-2-n-octylaminopropanol hydrochloride.

3. A pharmaceutical composition comprising from 5–900 mg of at least one compound selected from the group consisting of 1-(4-isopropylthiophenyl)-2-n-octylaminopropanol and its non-toxic salt together with at least one suitable excipient.

* * * * *